United States Patent
Kim

(10) Patent No.: US 10,893,907 B2
(45) Date of Patent: Jan. 19, 2021

(54) MEDICAL SKIN WRINKLE IMPROVEMENT DEVICE USING PEAK OF LASER PULSE WAVE

(71) Applicant: You In Kim, Cheongju-si (KR)

(72) Inventor: You In Kim, Cheongju-si (KR)

(*) Notice: Subject to any disclaimer, the term of this patent is extended or adjusted under 35 U.S.C. 154(b) by 261 days.

(21) Appl. No.: 15/578,408

(22) PCT Filed: Dec. 21, 2015

(86) PCT No.: PCT/KR2015/014023
§ 371 (c)(1),
(2) Date: Nov. 30, 2017

(87) PCT Pub. No.: WO2017/026599
PCT Pub. Date: Feb. 16, 2017

(65) Prior Publication Data
US 2018/0214208 A1 Aug. 2, 2018

(30) Foreign Application Priority Data
Aug. 11, 2015 (KR) .................. 10-2015-0112921

(51) Int. Cl.
*A61B 18/00* (2006.01)
*A61B 18/20* (2006.01)
*A61B 17/00* (2006.01)

(52) U.S. Cl.
CPC .... *A61B 18/203* (2013.01); *A61B 2017/0019* (2013.01); *A61B 2017/00128* (2013.01);
(Continued)

(58) Field of Classification Search
CPC ............................ A61N 5/0616; A61B 18/203
See application file for complete search history.

(56) References Cited

U.S. PATENT DOCUMENTS 6,695,835 B2* 2/2004 Furuno ................ A61B 18/203
606/10
9,161,815 B2* 10/2015 Nevo ................... A61B 18/203
(Continued)

FOREIGN PATENT DOCUMENTS

JP 2002-253571 A 9/2002
KR 10-0698868 B1 3/2007
(Continued)

*Primary Examiner* — Rex R Holmes
*Assistant Examiner* — Sana Sahand
(74) *Attorney, Agent, or Firm* — Rabin & Berdo, P.C.

(57) ABSTRACT

The present invention relates to a medical skin wrinkle improvement device using a peak of a laser pulse wave, and more specifically, to a medical skin wrinkle improvement device using a peak of a laser pulse wave, thereby lowering the degree of carbonization of a skin tissue having the laser irradiated thereon, thus enhancing a skin generation effect and shortening recovery time. The present invention comprises: a main body (100) which has formed on the upper part thereof a holding groove (110) having a tablet computer (200) attached/detached thereto, and which has mounted therein a controller (120) for controlling a hand piece (300) and the tablet computer (200); the hand piece (300) which comprises a laser oscillation unit (320), an optical unit (330) and a laser scanner, the laser oscillation unit (320) generating a laser to be irradiated for skin treatment, the optical unit (330) irradiating, as a parallel light, the laser generated by the laser oscillation unit (320), and the laser scanner adjusting the irradiation location of the laser transferred from the optical unit (330); and the tablet computer (200) which is provided with data input and screen display functions by means of a touch screen method, and which remotely controls the main body (100) through the transmission/reception of a bi-directional wireless signal.

8 Claims, 7 Drawing Sheets

(52) U.S. Cl.
CPC ............ *A61B 2017/00185* (2013.01); *A61B 2017/00199* (2013.01); *A61B 2017/00212* (2013.01); *A61B 2017/00221* (2013.01); *A61B 2017/00761* (2013.01); *A61B 2018/0047* (2013.01); *A61B 2018/00595* (2013.01); *A61B 2018/00625* (2013.01); *A61B 2018/00642* (2013.01); *A61B 2018/00678* (2013.01); *A61B 2018/00708* (2013.01); *A61B 2018/202* (2013.01); *A61B 2018/20359* (2017.05); *A61B 2018/20553* (2017.05); *A61B 2018/205547* (2017.05)

(56) References Cited

U.S. PATENT DOCUMENTS

| | | | |
|---|---|---|---|
| 2001/0053907 A1* | 12/2001 | Ota | A61B 18/203 606/10 |
| 2002/0049432 A1* | 4/2002 | Mukai | A61B 18/203 606/9 |
| 2002/0120256 A1 | 8/2002 | Furuno et al. | |
| 2002/0183811 A1* | 12/2002 | Irwin | A61N 5/0616 607/94 |
| 2005/0203592 A1* | 9/2005 | Teichert | A61N 5/0619 607/88 |
| 2009/0247996 A1* | 10/2009 | Abe | A61F 9/008 606/4 |
| 2014/0018783 A1* | 1/2014 | Modi | A61B 18/203 606/9 |
| 2014/0324135 A1* | 10/2014 | Jones | A61N 5/0616 607/88 |
| 2017/0216090 A1* | 8/2017 | Kim | A61N 5/06 |

FOREIGN PATENT DOCUMENTS

| | | |
|---|---|---|
| KR | 10-0938378 B1 | 1/2010 |
| KR | 10-2013-0125154 A | 11/2013 |
| KR | 10-2014-0140393 A | 12/2014 |
| KR | 10-1558948 B1 | 10/2015 |
| KR | 101571533 B1 * | 11/2015 |

* cited by examiner

MEDICAL SKIN WRINKLE IMPROVEMENT DEVICE USING PEAK OF LASER PULSE WAVE

TECHNICAL FIELD

The present invention relates to a medical skin wrinkle improvement device using a peak of a laser pulse wave. More particularly, the present invention relates to a medical skin wrinkle improvement device able to improve skin regenerative effect and reduce recovery time by lowering the degree of carbonization of a skin tissue irradiated by a laser beam using the peak of the laser pulse wave.

BACKGROUND ART

Recently, in response to improvements in the quality of life, an era in which interest in skin health and appearance is highlighted more than ever has come. Regardless of age, people may attempt to obtain smooth baby-like skin by peeling a single layer of the skin. Skin peeling treatment is a medical treatment based on plastic surgery that can actually realize baby-like skin.

Skin peeling treatment actually removes a thin layer of the skin. The effect of skin peeling treatment is more significant as skin peeling is performed more deeply. However, skin peeling leads to significant side effects and requires a significant amount of time for the skin to recover. Thus, fractional laser treatment has been introduced, since this treatment can significantly reduce side effects while achieving effects similar to those of skin peeling treatment.

Fractional laser treatment stimulates collagen underlying the dermis by forming a plurality of microscopic holes in the skin surface using a laser. This can induce rearrangement in a skin layer, thereby regenerating a new skin layer that is smooth like a baby's skin. Keratin-forming cells in regions, onto which the laser beam is not irradiated, rapidly move into the microscopic holes, formed by the laser beam, thereby improving the recovery rate and reducing wrinkles.

Recently, methods to increase the density of a laser spot have been attempted in order to improve the skin regenerative effect of fractional laser treatment. However, when the density of a laser spot is excessively increased, the skin regenerative effect is lowered. Since the skin is exposed to high-temperature heat due to a laser beam, when cells irradiated by the laser beam are exposed to another laser beam without a sufficient amount of time for cooling, there is a danger in that the cells may be burned. Therefore, fractional laser treatment requires a new approach for improving skin regeneration efficiency and reducing recovery time.

DISCLOSURE

Technical Problem

Accordingly, the present invention has been made keeping in mind the above problems occurring in the prior art, and an object of the present invention is to provide a medical skin wrinkle improvement device using a peak of a laser pulse wave. When the amplitude of a laser pulse wave reaches a preset steady state value after having reached a peak, the generation of the laser pulse wave is stopped. It is thereby possible to lower the degree of carbonization of a skin tissue irradiated by the laser beam, based on the peak of the laser pulse wave, and improve a skin regenerative effect.

Another object of the present invention is to provide a medical skin wrinkle improvement device using a peak of a laser pulse wave, the device including a pulse width controller controlling a time width of the laser pulse wave; and a steady state setter setting a steady state amplitude of the laser pulse wave.

Another object of the present invention is to provide a medical skin wrinkle improvement device using a peak of a laser pulse wave, in which a pulse radiation number setter controlling the number of bursts of the laser pulse wave is provided.

Another object of the present invention is to provide a medical skin wrinkle improvement device using a peak of a laser pulse wave, in which a laser pulse amplitude controller adjusting an intensity level of laser radiation by controlling the amplitude of the laser pulse wave is provided.

Another object of the present invention is to provide a medical skin wrinkle improvement device using a peak of a laser pulse wave, in which the laser scanner includes an X-axis rotating mirror, an X-axis control motor adjusting an angle of the X-axis rotating mirror, a Y-axis rotating mirror, and a Y-axis control motor adjusting an angle of the Y-axis rotating mirror. The laser scanner changing coordinates of the laser beam to irradiate an intended position of a treatment site.

Another object of the present invention is to provide a medical skin wrinkle improvement device using a peak of a laser pulse wave, in which a laser power level lamp emitting a variety of colors of light depending on power levels of the laser beam in order to prevent an operator or a surgeon from mistakenly determining the power levels of the irradiating laser beam is provided.

Technical Solution

In order to accomplish the above object, the present invention provides a medical skin wrinkle improvement device. The medical skin wrinkle improvement device may include: a main body having a fitting recess into which a tablet computer is detachably fitted and a controller is disposed therewithin, the controller controlling a handpiece and the tablet computer; the handpiece including a laser oscillator generating a laser beam to irradiate skin for a treatment, an optical unit transferring the laser beam, generated by the laser oscillator, as collimated light, and a scanner adjusting a position to be irradiated by the laser beam, transferred by the optical unit; and the tablet computer having data input and screen display functions based on a touchscreen interface and configured to remote control the main body by transmitting receiving bidirectional wireless signals. When an amplitude of a laser pulse wave reaches a preset steady value after having reached a peak, the controller stops generation of the laser pulse wave to lower a degree of carbonization of skin tissue irradiated by the laser beam based on the peak of the laser pulse wave, thereby improving a skin regenerative effect and reducing a recovery time.

The controller may include: a pulse width controller controlling a time width of the laser pulse wave; and a steady state setter setting a steady state amplitude of the laser pulse wave.

The controller may include a pulse radiation number setter controlling the number of bursts of the laser pulse wave.

The controller may include a laser pulse amplitude controller adjusting an intensity level of laser radiation by controlling an amplitude of the laser pulse wave.

The laser scanner may include: an X-axis rotating mirror; an X-axis control motor adjusting an angle of the X-axis rotating mirror; a Y-axis rotating mirror; and a Y-axis control motor adjusting an angle of the Y-axis rotating mirror, the laser scanner changing coordinates of the laser beam to irradiate an intended position of a treatment site.

The handpiece may include: a rubber clamp having an outer surface including an upper cover case and a lower cover case, which are engageable with and disengageable from each other, and the rubber clamp surrounding the laser oscillator to protect the laser oscillator; a laser scanner coupled to one end of the rubber clamp to adjust the position to be irradiated by the laser beam; an optical unit including a plurality of collimated light lenses to radiate the laser beam, guided by the laser scanner, as collimated light; and a handpiece tip coupled to one end of the optical unit to obtain a predetermined distance between the optical unit and a skin.

The controller may include a laser power level lamp emitting a variety of colors of light depending on power levels of the laser beam in order to prevent an operator or a surgeon from mistakenly determining the power levels of the radiated laser beam.

Advantageous Effects

As described above, according to the present invention, when the amplitude of a laser pulse wave reaches a preset steady state value after having reached a peak, the generation of the laser pulse wave is stopped. It is thereby possible to lower the degree of carbonization of a skin tissue irradiated by the laser beam, based on the peak of the laser pulse wave, and improve a skin regenerative effect.

In addition, according to the present invention, the pulse width controller controlling a time width of the laser pulse wave and a steady state setter setting a steady state amplitude of the laser pulse wave are provided, such that the peak of the laser pulse wave is used in skin treatment.

Furthermore, according to the present invention, the pulse radiation number setter controlling the number of bursts of the laser pulse wave is provided to adjust the number of bursts of the laser pulse wave.

In addition, according to the present invention, the laser pulse amplitude controller controlling the amplitude of the laser pulse wave is provided to adjust the intensity level of laser radiation.

Furthermore, according to the present invention, the X-axis rotating mirror, the X-axis control motor adjusting the angle of the X-axis rotating mirror, the Y-axis rotating mirror, and the Y-axis control motor adjusting the angle of the Y-axis rotating mirror are provided in order to change coordinates of the laser beam to irradiate an intended position of a treatment site.

In addition, according to the present invention, the laser power level lamp emitting a variety of colors of light depending on power levels of the laser beam is provided in order to prevent an operator or a surgeon from mistakenly determining the power levels of the irradiating laser beam is provided.

The above and other detailed effects of the present invention will be understood from the following detailed description of the mode for invention section.

BEST MODE

The present invention provides a medical skin wrinkle improvement device including: a main body having a fitting recess into which a tablet computer is detachably fitted and a controller disposed therewithin, the controller controlling a handpiece and the tablet computer; the handpiece comprising a laser oscillator generating a laser beam to irradiate the skin for treatment, an optical unit transferring the laser beam, generated by the laser oscillator, as collimated light, and a scanner adjusting a position to be irradiated by the laser beam, transferred by the optical unit; and the tablet computer having data input and screen display functions based on a touchscreen interface and configured to remote control the main body by transmitting receiving bidirectional wireless signals. When the amplitude of a laser pulse wave reaches a preset steady value after having reached a peak, the controller stops generation of the laser pulse wave to lower a degree of carbonization of skin tissue irradiated by the laser beam based on the peak of the laser pulse wave, thereby improving a skin regenerative effect and reducing a recovery time.

MODE FOR INVENTION

Hereinafter, exemplary embodiments of the present invention will be described in detail with reference to the accompanying drawings.

The embodiments of the present invention may be modified in many different forms and the scope of the invention should not be limited to the embodiments set forth herein. Rather, these embodiments are provided so that this disclosure will be thorough and complete, and will fully convey the concept of the invention to those skilled in the art.

Figure 1:
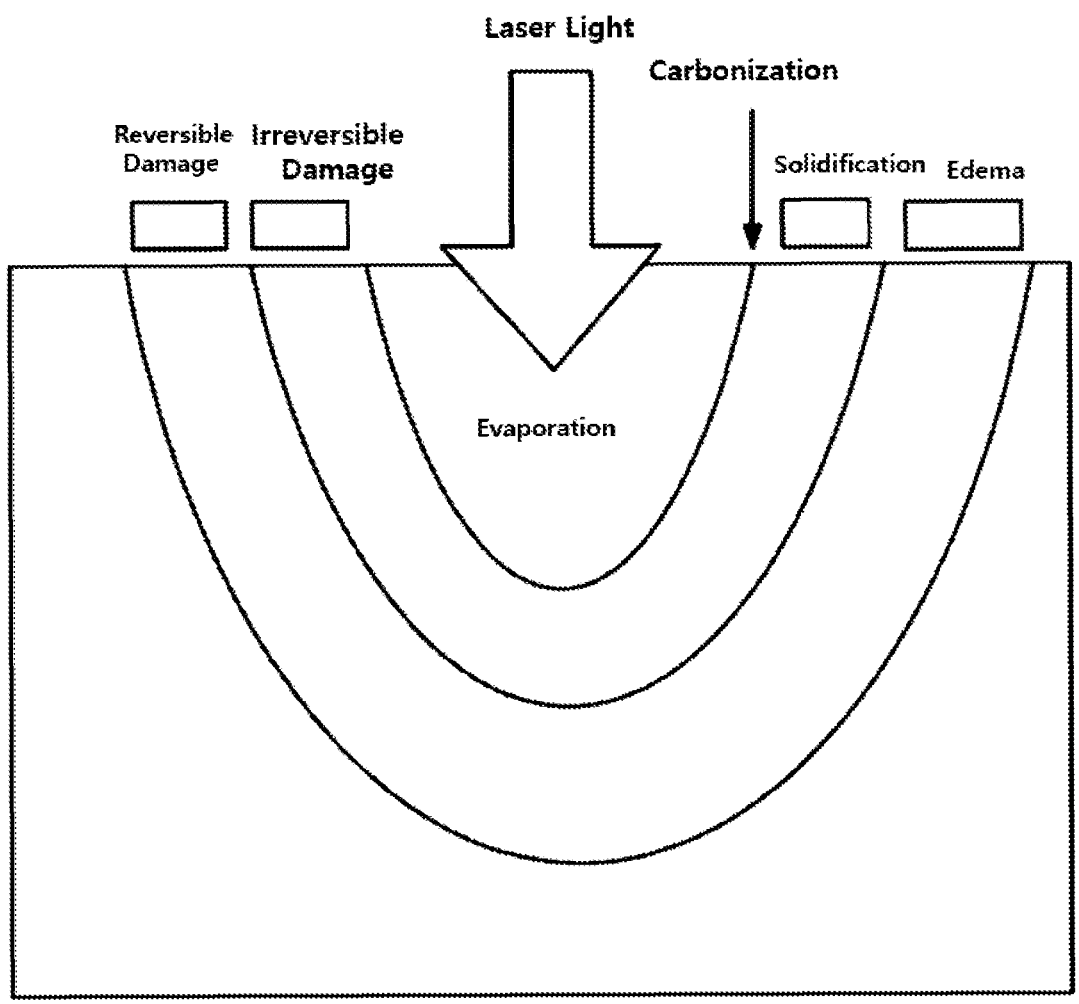
FIG. 1 is a diagram illustrating the state of a skin tissue right after irradiated by a laser beam.

FIG. 1 is a diagram illustrating the state of a skin tissue right after irradiated by a laser beam. When the skin tissue is irradiated by the laser beam, a spot irradiated by the laser beam is evaporated by high-temperature heat generated by the laser beam, so that a microscopic hole is formed in the skin tissue. Heat is transferred through the hole, formed as described above, to stimulate collagen underlying the dermis. This can consequently cause rearrangement in the skin layer, thereby causing regeneration in the skin. Keratin-forming cells in regions where the laser beam is not radiated rapidly move into the microscopic hole, formed by the laser beam, thereby improving the recovery rate and reducing wrinkles.

Due to photothermal and photochemical actions occurring during irradiation by the laser beam onto the skin tissue, a carbonized layer is formed in the surface of the hole, a solidification layer, i.e. an irreversibly damaged portion, is formed outside of the carbonized layer, and an edema layer, i.e. a reversibly damaged portion, is formed outside of the solidification layer.

In this case, the carbonized layer formed as described above degrades the regenerative effect. In addition, the carbonized layer increases post-inflammatory hyperpigmentation (PIH) and recovery time (D), acting as an obstacle to fractional laser surgery. Thus, the present invention is intended to reduce the degree of carbonization of the laser irradiated surface in order to improve the skin regenerative effect and reduce the recovery time.

Figure 3:
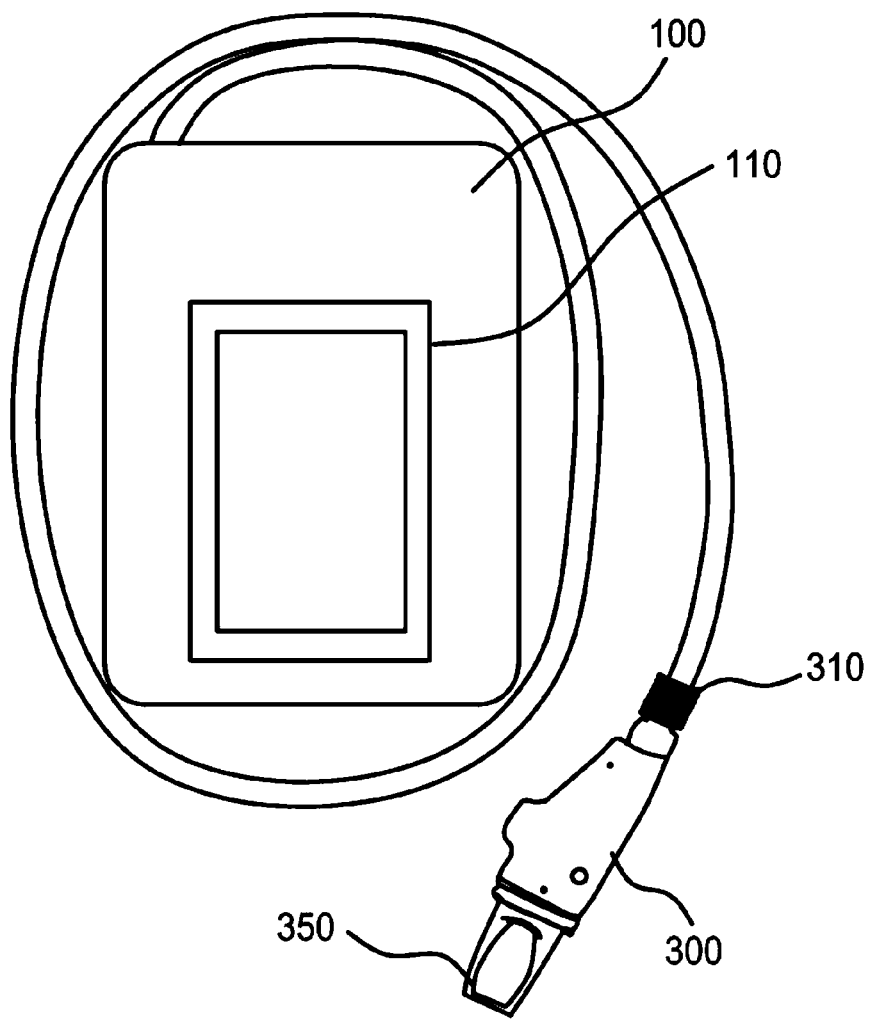
FIG. 3 is a plan view of the medical laser according to the present invention.
Figure 4:
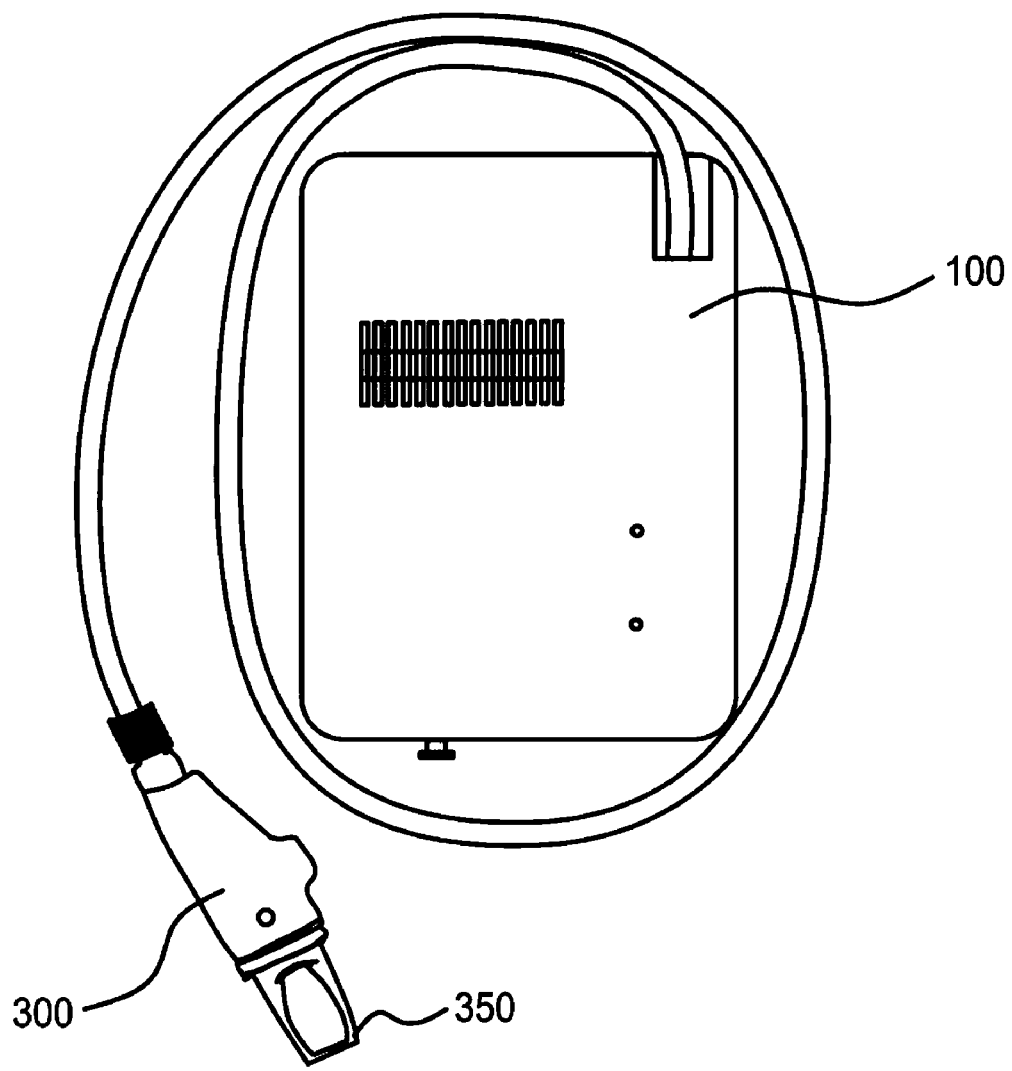
FIG. 4 is a bottom view of the medical laser according to the present invention.
Figure 5:
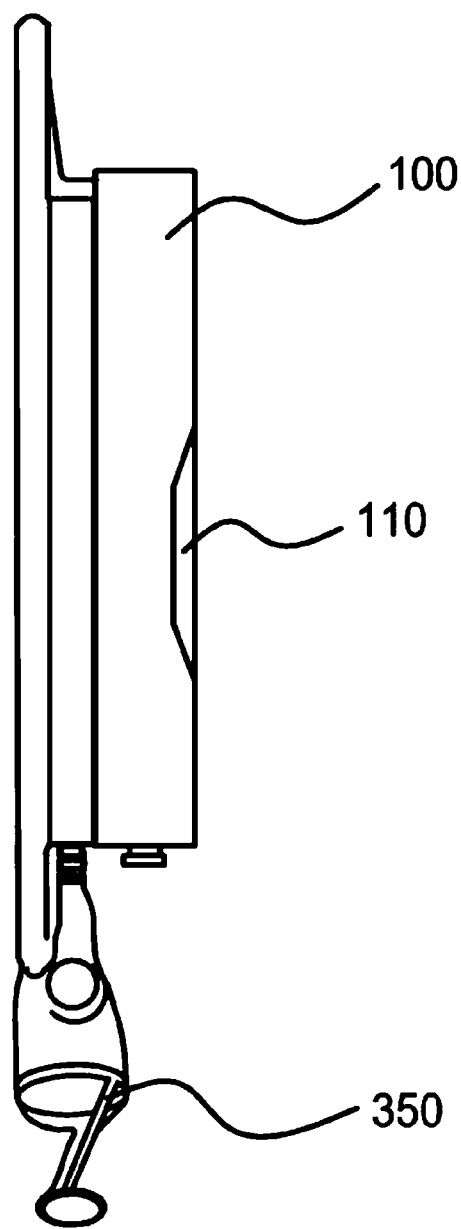
FIG. 5 is a side elevation view of the medical laser according to the present invention.
Figure 6:
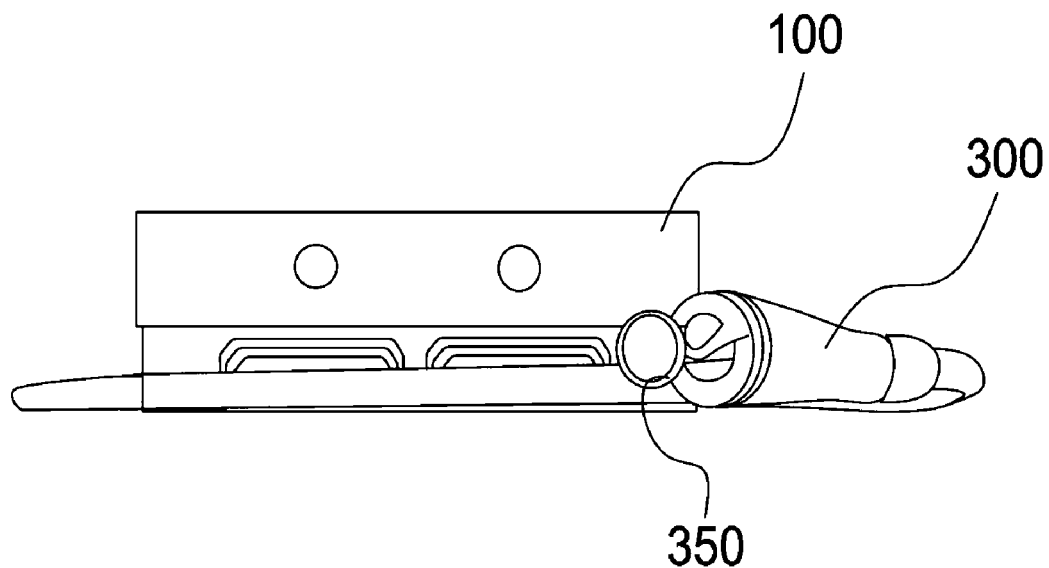
FIG. 6 is a front elevation view of the medical laser according to the present invention.
Figure 7:
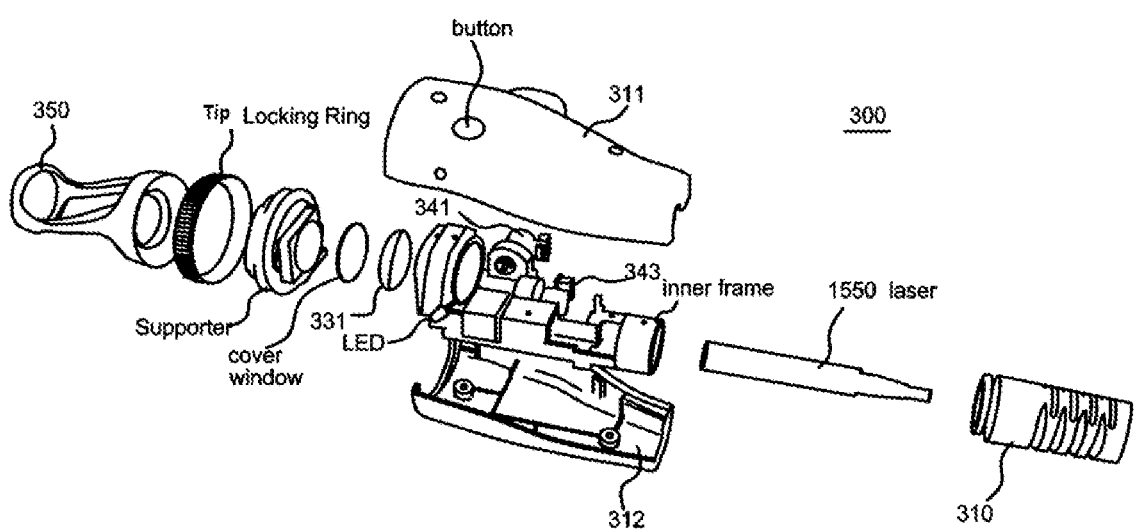
FIG. 7 is an exploded view of the handpiece of the medical laser according to the present invention.

FIG. 3 is a plan view of the medical laser according to the present invention, FIG. 4 is a bottom view of the medical laser according to the present invention, FIG. 5 is a side elevation view of the medical laser according to the present invention, FIG. 6 is a front elevation view of the medical laser according to the present invention, and FIG. 7 is an exploded view of a handpiece 300 of the medical laser according to the present invention.

The medical laser according to the present invention includes a main body 100 within which a controller 120 is disposed, a handpiece 300, and a tablet computer 200.

Figure 2:
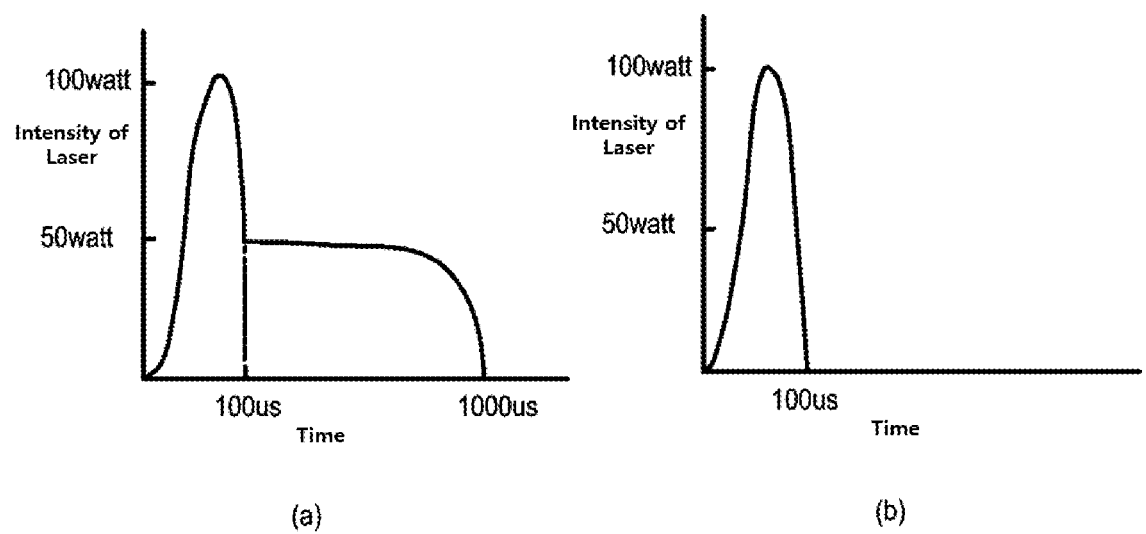
FIG. 2a is a graph illustrating a laser pulse wave used in a medical laser of the related art.
FIG. 2b is a graph illustrating a laser pulse wave used in a medical laser according to the present invention.

FIG. 2a is a graph illustrating a laser pulse wave used in a medical laser of the related art, while FIG. 2b is a graph illustrating a laser pulse wave used in the medical laser according to the present invention.

FIG. 2a illustrates a typical pulse wave of an erbium (Er) glass laser beam. At an early stage in which a laser beam is generated, the pulse wave reaches a peak of about 100 watts, and then, a steady state of about 50 watts after 100 us. After the steady state has been maintained, power is turned off at 1000 us, so that one cycle is completed.

According to the present invention, only a peak value of the pulse wave was used to reduce the degree of carbonization of the laser irradiated surface. FIG. 2b illustrates the laser pulse wave used in the medical laser according to the present invention.

When the amplitude of the laser pulse wave reaches the preset steady value from the peak, the controller 120 according to the present invention stops the generation of the laser pulse wave. Thus, only the peak of the laser pulse is allowed to be radiated to the skin tissue.

The controller 120 includes a steady state setter 122 and a pulse width controller 121. The steady state setter 122 sets a steady state amplitude of a laser pulse wave. The pulse width controller 121 controls a time width of the pulse wave by controlling the generation of the laser pulse wave when the amplitude of the laser pulse wave reaches the preset steady state from the peak.

The use of the peak of the laser pulse wave increases the number of laser bursts per unit time, compared to the use of the laser pulse wave including the steady state. In this regard, the controller 120 includes a pulse burst number setter 123 to control the number of bursts of the laser pulse wave.

In addition, the controller 120 includes a laser pulse amplitude controller 124 to control the amplitude of a laser pulse in order to adjust the intensity of laser radiation.

The controller 120 includes a laser power level lamp 125. The laser power level lamp 125 emits a variety of colors of light depending on the power levels of laser beams in order to prevent an operator or a surgeon from mistakenly determining the power levels of irradiated laser beams.

Figure 8:
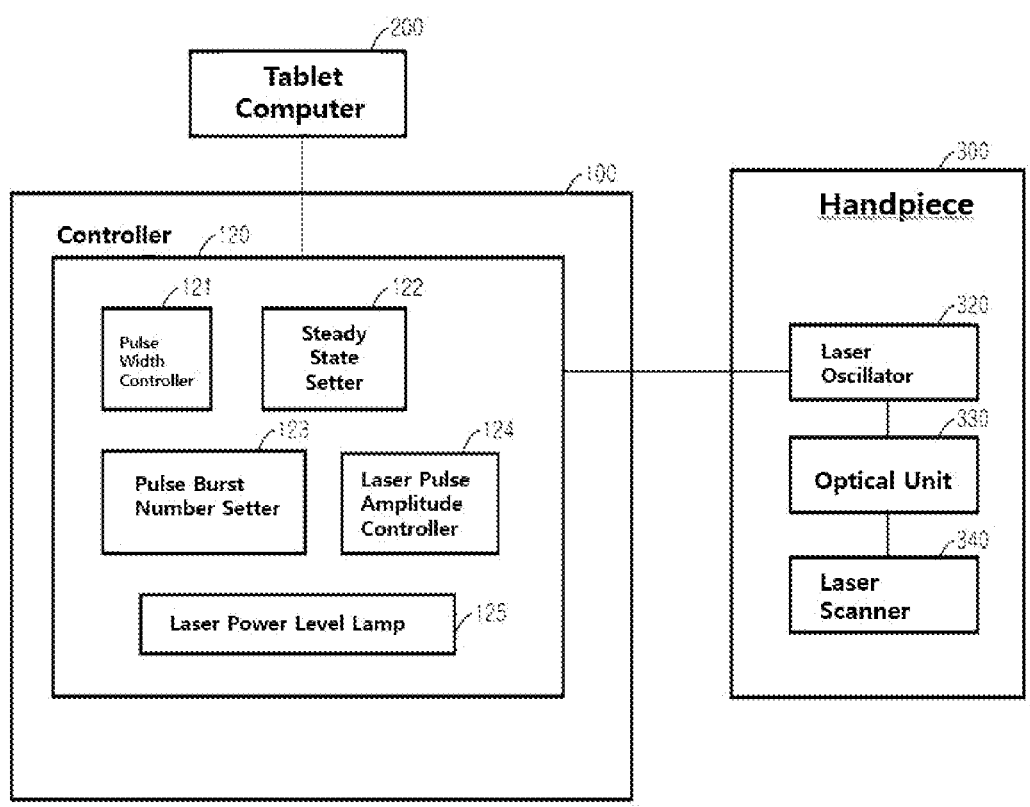
FIG. 8 is a block diagram of the medical laser according to the present invention.

FIG. 8 is a block diagram of the medical laser according to the present invention. The controller 120 according to the present invention controls the handpiece 300 and the tablet computer 200. The controller 120 includes the pulse width controller 121, the steady state setter 122, the pulse burst number setter 123, and the laser pulse amplitude controller 124 to control a variety of design variables of the laser pulse wave.

The main body 100 has a fitting recess 110 into which the tablet computer 200 is detachably fitted, and the controller 120 controlling the handpiece 300 and the tablet computer is disposed within the main body 100.

The handpiece 300 is a device configured to be brought into close contact with a treatment site of a patient to directly irradiate the treatment site. The handpiece 300 is connected to the main body 100 through an optical cable to generate a laser beam and directly irradiate the treatment site. The handpiece 300 includes a laser oscillator 320 generating a laser beam to irradiate a portion of the skin for treatment, an optical unit 330 transferring the laser beam, generated by the laser oscillator 320, as collimated light, and a scanner 340 adjusting a position to be irradiated by the laser beam, transferred by the optical unit 330.

The handpiece 300 includes a rubber clamp 310, a laser scanner 340, an optical unit 330, and a handpiece tip 350. The outer surface of the rubber clamp 310 is comprised of an upper cover case 311 and a lower cover case 312, which are engaged with each other. The rubber clamp 310 surrounds the laser oscillator 320 to protect the laser oscillator 320. The laser scanner 340 is coupled to one end of the rubber clamp 310 to adjust a position to be irradiated by a laser beam. The optical unit 330 is comprised of a plurality of collimated light lenses 331 to radiate the laser beam, guided by the laser scanner 340, as collimated light. The handpiece tip 350 is coupled to one end of the optical unit 330 to obtain a predetermined distance between the optical unit 330 and the skin.

The laser oscillator 320 generates an Er glass laser beam. The laser oscillator 320 is a device generating a laser beam to irradiate a treatment site of a patient so as to form a microscopic hole in a skin tissue.

The optical unit 330 is a device converting the laser beam, generated by the laser oscillator 320, into collimated light. The optical unit 330 includes a collimation correction lens to generate and output collimated light.

The laser scanner 340 is configured to radiate a laser beam transferred by the optical unit 330 onto a treatment site of a patient, and has a function of controlling coordinates of the position to be irradiated by the laser beam. Specifically, the laser scanner includes an X-axis rotating mirror 341, an X-axis control motor 342 adjusting the angle of the X-axis rotating mirror 341, a Y-axis rotating mirror 343, and a Y-axis control motor 344 adjusting the angle of the Y-axis rotating mirror 343. The laser scanner can variously change the position coordinates of the laser beam to irradiate the treatment site.

The tablet computer 200 can provide data input and screen display functions based on a touchscreen interface. The tablet computer 200 can receive a variety of input set values regarding laser radiation, as well as display a process of radiating a laser beam. In addition, the tablet computer 200 may include a CPU and a memory disposed therein to perform calculation and store data.

In addition, the tablet computer 200 is configured to be attachable to and detachable from the fitting recess 110 of the main body 100 to provide portability and mobility to the tablet computer 200 or the main body 100.

Although the present invention has been described for illustrative purposes, those skilled in the art will appreciate that various modifications, additions and substitutions are possible, without departing from the scope and spirit of the present invention as disclosed in the accompanying claims. Although functions and effects obtainable from configurations of the present invention have not been explicitly described when the foregoing embodiments of the present invention were described, it should be understood that any effects conceivable from such configurations shall be regarded the effects of the present invention.

What is claimed is:

1. A medical skin wrinkle improvement device comprising:
   a main body;
   a handpiece; and
   a tablet computer,
   wherein:
   a controller is disposed within the main body;
   the main body has a fitting recess into which the tablet computer is detachably fitted;
   the handpiece comprises a laser oscillator generating a laser beam to irradiate skin for a treatment, a lens device configured to convert the laser beam, generated by the laser oscillator, into collimated light, and a laser scanner configured to radiate a laser beam transferred by the lens device onto a treatment site, and the laser scanner includes an X-axis rotating mirror, an X-axis control motor configured to adjust an angle of the X-axis rotating mirror, a Y-axis rotating mirror, and a Y-axis control motor configured to adjust an angle of the Y-axis rotating mirror to change coordinates of the laser beam to irradiate an intended position of the treatment site; and
   the tablet computer having data input and screen display functions based on a touchscreen interface and configured to remotely control the main body by transmitting and receiving bidirectional wireless signals, wherein
   the controller includes a steady state setter configured to set a steady state amplitude of the laser pulse wave,
   the controller controls an amplitude of a laser pulse in order to adjust intensity of laser radiation, and
   in response to detection of the amplitude of the laser pulse wave having reached a preset steady value corresponding to the steady state amplitude after having reached a peak, the controller stops generation of the laser pulse wave, such that generating of the laser pulse wave is discontinued at a moment of the laser pulse wave reaching the preset steady value from the peak without maintaining the preset steady value of the amplitude, and wherein
   the controller includes a laser power level lamp which emits a variety of colors of light depending on power levels of irradiated laser beams in order to prevent a mistaken determination of the power levels of the irradiated laser beams.

2. The medical skin wrinkle improvement device according to claim 1, wherein the controller comprises:
   a pulse width controller controlling a time width of the laser pulse wave.

3. The medical skin wrinkle improvement device according to claim 1, wherein the controller comprises a pulse burst number setter controlling a number of bursts of the laser pulse wave.

4. The medical skin wrinkle improvement device according to claim 1, wherein the controller comprises a laser pulse amplitude controller adjusting an intensity level of laser radiation by controlling an amplitude of the laser pulse wave.

5. The medical skin wrinkle improvement device according to claim 1, wherein the handpiece comprises:
   a rubber clamp having an outer surface including an upper cover case and a lower cover case, which are engageable with and disengageable from each other, and the rubber clamp surrounding the laser oscillator to protect the laser oscillator;
   a laser scanner coupled to one end of the rubber clamp to adjust the position to be irradiated by the laser beam; and
   a handpiece tip coupled to one end of the optical unit to obtain a predetermined distance between the optical unit and a skin.

6. The medical skin wrinkle improvement device according to claim 1, wherein a period of time of the amplitude being at the peak is shorter than a period of time during which the amplitude falls from the peak to zero.

7. The medical skin wrinkle improvement device according to claim 1, wherein the amplitude declines from the peak directly after having reached the peak.

8. The medical skin wrinkle improvement device according to claim 1, wherein the fitting recess forms an opening in an outer surface of the main body.

* * * * *